United States Patent
Balasubramanian et al.

(10) Patent No.: US 7,351,688 B2
(45) Date of Patent: Apr. 1, 2008

(54) COMPOSITIONS AND METHODS FOR LESS IMMUNOGENIC PROTEIN FORMULATIONS

(75) Inventors: Sathyamangalam V. Balasubramanian, Amherst, NY (US); Robert M. Straubinger, Amherst, NY (US); Vivek S. Purohit, Fort Erie (CA); Karthik Ramani, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 11/049,134

(22) Filed: Feb. 2, 2005

(65) Prior Publication Data

US 2005/0227913 A1 Oct. 13, 2005

Related U.S. Application Data

(63) Continuation-in-part of application No. 10/773,075, filed on Feb. 5, 2004, now abandoned.

(60) Provisional application No. 60/445,134, filed on Feb. 5, 2003.

(51) Int. Cl.
*A61K 38/00* (2006.01)

(52) U.S. Cl. ....................................................... 514/2

(58) Field of Classification Search ................ 530/350; 514/12; 435/7.1
See application file for complete search history.

(56) References Cited

U.S. PATENT DOCUMENTS

| | | | |
|---|---|---|---|
| 4,127,502 | A | 11/1978 | Li Mutti et al. |
| 4,795,806 | A | 1/1989 | Brown et al. |
| 5,580,856 | A | 12/1996 | Prestrelski et al. |
| 6,593,294 | B1 | 7/2003 | Baru et al. |
| 2002/0098192 | A1 | 7/2002 | Whitlow et al. |
| 2002/0132982 | A1 * | 9/2002 | Balasubramanian et al. ................. 530/350 |
| 2003/0118539 | A1 | 6/2003 | Fahl et al. |
| 2003/0176331 | A1 | 9/2003 | Rosenblum et al. |

2004/0229793 A1 11/2004 Balasubramanian et al.

FOREIGN PATENT DOCUMENTS

WO WO 99/55306 * 11/1999

OTHER PUBLICATIONS

Aguilar et al., Phospholipid membranes form specific nonbilayer molecular arrangements that are antigenic, Sep. 1999, J Biol Chem., vol. 274, No. 36, pp. 25193-25196.*
Kirby et al. Preparation of liposomes containing Factor VIII for oral treatment of haemophilia. Journal of Microencapsulation. Jan. 1984, vol. 1 No. 1, pp. 33-45.
Lenting, P.J., et al., *The light chain factor VIII comprises a binding site for low density lipoprotein receptor-related protein*; The Journal of Biological Chemistry, Aug. 1999, vol. 274, No. 34, pp. 23734-23739.
Raut, et al., *Phospholipid binding of factor VIII in different therapeutic concentrates*; British Journal of Hematology, 1999, vol. 107, pp. 323-329.
Mark C. Manning, et al., Stability of Protein Pharmaceuticals; Pharmaceutical Research, vol. 6, No. 11, 1989, pp. 903-918, Plenum Publishing Corporation.
Sathyamangalam V. Balasubramanian, et al., Liposomes as Formulation Excipients for Protein Pharmaceuticals: A Model Protein Study; Pharmaceutical Research, vol. 17, No. 3, 2000, pp. 344-350, Plenum Publishing Corporation.
Andrea Braun,et al., Protein Aggregates Seem to Play a Key Role Among the Parameters Influencing the Antigenicity of Interferon Alpha (IFN-α) in Normal and Transgenic Mice; Pharmaceutical Research, vol. 14, No. 10, 1997, pp. 1472-1478, Plenum Publishing Corporation.

* cited by examiner

*Primary Examiner*—Robert B. Mondesi
(74) *Attorney, Agent, or Firm*—Hodgson Russ LLP (57) ABSTRACT

Methods and composition are described for low immunogenic protein, polypeptide or peptide formulations. The method comprises forming complexes of the protein, polypeptide or peptide with a binding agent which can be a serine containing compound or other phosphatidyl compounds or phospholipids. The complexes formed include simple complexes, micelles, cochleate structures, liposomes, non-bilayer and novel lipidic structures. The antigenicity and imminogenicity of the protein, polypeptides or peptides is reduced upon formation of such complexes.

1 Claim, 11 Drawing Sheets

COMPOSITIONS AND METHODS FOR LESS IMMUNOGENIC PROTEIN FORMULATIONS

This application is a continuation-in-part of U.S. Nonprovisional application No. 10/773,075 filed on Feb. 5, 2004, now abandoned, which in turn claims priority to U.S. provisional patent application No. 60/445,134 filed on Feb. 5, 2003, the disclosures of which are incorporated herein by reference.

This invention was made with Government support under grant no. RO1HL-70227-01 from the National Institutes of Health. The Government has certain rights in the invention.

FIELD OF THE INVENTION

The present invention relates to protein complexes having low immunogenicity and a method of making same.

DISCUSSION OF RELATED ART

Hemophilia is a bleeding disorder caused by the deficiency of factor VIII (anti hemophilic factor, AHF or FVIII). FVIII is a multi domain protein comprising of six domains A1, A2, A3, B, C1 and C2 and activation of this protein by thrombin results in heavy (A1 and A2) and light chain (A3, C1 and C2) [1, 2]. Replacement therapy using blood concentrate, recombinant factor VIII and variants of factor VIII is the first line therapy for hemophilia. However, 15-35% of patients develop neutralizing antibodies and such immune response compromises therapy for hemophilia. Current treatment regimens to overcome neutralizing antibody development exist but are not cost effective. Development of less immunogenic Factor VIII preparations could offer an alternate clinical approach.

In general, it has been shown that the immune response to a therapeutic protein is due to the following reasons; (i) route of administration, (ii) existence of aggregates, (iii) frequent administration and (iv) specific epitope regions [3]. Recently, it has been shown that FVIII has a tendency to form aggregates [4] and the role of these aggregates in the development of immune response is not well understood. Further, there are primarily two epitope regions on FVIII molecule, C2 and A2 domains. Scandella et al [5] has shown that the antibody titre is highest against the C2 domain of the light chain. The C2 domain is also a membrane binding domain and it binds to phosphatidyl serine (PS) on platelet membranes as part of its coagulation cascade [6,7]. The anticoagulant action of antibodies to the C2 domain is due to inhibition of binding of factor VIII to phospholipid. It has been shown that the monoclonal antibodies against the C2 domain prevent the binding of Factor VIII to phospholipid containing membranes and based on these observations it was concluded that the epitope and membrane binding regions overlap [10, 11].

Previous studies on liposomal encapsulation of FVIII were aimed at increasing the encapsulation efficiency of FVIII (Factor VIII) in conventional liposomes and further to increase the in vivo stability and oral bioavailability [12, 13]. Due to the molecular architecture, lipid molecules tend to form several molecular assemblies such as liposomes, micelles, non-bilayer structures and cochleate structures. Extensive studies have been done to use these molecular assemblies as drug delivery vehicles to improve the therapeutic properties of several drugs including proteins and peptides. These therapeutic properties are prolonging circulation time, reducing the toxicity, enhancement of immune response and reduction of in vivo degradation [14-25]. Thus, liposomes have been used as adjuvants to increase the immune response [26-31]. However, development of lipid complex to reduce immune response and antigenicity has not been investigated and therefore, there continues to be a need to develop approaches for reducing the immunogenicity of therapeutic proteins. Another approach has been to modify the sequence of the specific epitopes to reduce immuno toxicity [32]. However, such amino acid substitutions could lead to loss of biological activity.

SUMMARY OF THE INVENTION

The present invention discloses compositions having low antigenicity and immunogenicity and methods of making same. Accordingly, compositions comprising a therapeutic agent such as a protein, polypeptide or peptide and one or more molecules capable of binding to the protein (referred to herein as the binding agent) in such a way as to reduce its immunogenicity and antigenicity are disclosed. Such binding agents include serine compounds such as phosphoserine, phosphatidyl serine, or phospholipids comprising phosphatidyl serine (PS); phosphatidyl choline (PC), phospatidic acid (PA), or phosphoethanolamine (PE); or phospholipids containing PA, PC, or PE.

The protein-binding agent complexes can be in the form of (1) liquid or freeze dried form of this liquid containing protein-binding agent complex (2) novel non-liposomal structures, (3) liposomes (4) micelles (5) cochleate (6) non-bilayer structures which reduce the immune response.

The present invention also discloses a method for reducing the immunogenicity and/or antigenicity of a protein by forming a complex with a binding agent (such as a serine containing compound). The protein-binding agent complex may be stabilized with suitable buffers.

In one embodiment, the dried lipid film containing dimyristyl phosphatidyl choline (DMPC) and brain phosphatidyl serine (bPS) is hydrated using protein (such as FVIII) in various buffer systems. Novel, non liposomal structures are formed using DMPC, bPS in 300 mM NaCl and 5 mM $CaCl_2$. Conventional liposomes are formed as the buffer system is changed to water or phosphate buffered saline. This can also be accomplished by reducing the calcium or PS concentrations. The removal of DMPC and using 100% PS and a sonication or extrusion step leads to cochleate structures and use of PS with intermediate acyl chain length results in micellar structures. Use of shorter acyl chain length at lower concentrations yield protein-lipid complexes in solution.

DETAILED DESCRIPTION OF THE INVENTION

The terms AHF, Factor VIII and FVIII are used interchangeably to mean the same molecule.

The present invention provides a method for reducing the antigenicity and immunogenicity of proteins. While the term "protein" is used throughout the application, it is intended to include peptides (generally considered to be 50 or less amino acids) as well as polypeptides (generally considered to be more than 50 amino acids).

The method of the present invention comprises the steps of forming complexes of one or more proteins, polypeptides or peptides with a phospholipid, preferably a phospholipid containing serine. Various types of protein-lipid structures can be formed depending upon the particular phospholipid, concentration and combinations of phospholipids In general, the term "Liposome" means a generally spherical or spheroidal cluster or aggregate of lipid compounds, typically in the form of one or more concentric layers, for example, monolayers, bilayers or multi-layers. They may also be referred to as lipid vesicles. The liposomes may be formulated, for example, from ionic lipids and/or non-ionic lipids.

The terms "Cochleates" or "cochleate sturcutres" generally refer to a multilamellar lipid vesicle that is generally in the shape of a spiral or a tubule.

The term "Micelles" refers to colloidal entities formulated from lipids. Micelles may comprise a monolayer, bilayer, or hexagonal phase structure.

In the present invention it was observed that different structures were formed with the protein/polypeptide complexes depending upon the binding agent. In general, if serine containing agents were used, simple complexes, micelles, liposomes, cochleate structures and novel condensate phase were observed. If other phosphatidyl compounds or phospholipids were used (such as PC, PG, PA or PE or phospholipids containing PC, PG or PE), only micelles or liposomes were observed. Further, only PE containing phospholipids were observed to form bilayer and non-bilayer (hexagonal) structures.

The use of phosphoserine, phosphatidyl serine, or PS containing phospholipids with short acyl chain length (i.e, with 4 or less acyl chain carbon atoms) did not lead to the formation of lipid molecular assemblies. The structures formed are simple complexes. These simple complexes are characterized by mostly ionic bonding. Use of serine containing phospholipids having intermediate acyl chain length (i.e., between 5-12 acyl chain carbon atoms) above its critical micellar concentration, form micelles and below critical micellar concentration form simple complexes. The phospholipids having longer acyl chain length (12-18 carbon atoms), due to the molecular architecture, tend to form several molecular assembles such as liposomes, non-bilayer structures and cochleate structures.

The use of other phosphatidiyl compounds such as PC, PG, PA and PE and phospholipids containing PC, PG, PA and PE results in the formation of micelles for intermediate length acyl chain carbon atoms and liposomes for longer length acyl chain carbon atoms.

In all the phospholipids the acyl chain may be a diacyl chain or a single acyl chain. The term phosphatidyl serine, phosphatidyl choline, phosphatidyl ethanolamine, phosphatidyl glycerol means there is no acyl chain in the compound.

The lipid composition may be varied to prepare liposome, non-bilayer structures and cochleate phases. A lipid composition of phosphatidyl choline (PC): phsophatidyl serine (PS) or phosphoserine with high PC content will form liposomes upon hydration with buffers containing $Ca^{2+}$ and $Na^{+}$. The presence of Phosphatidyl Ethanolamine PE and PS promote the formation of non-bilayer structures. The formulation with PS (over 90 mol %) in the presence of $Ca^{2+}$ with no or lower $Na^{+}$ (100 mM) promote the formation of cochleate cylinders. Conditions such as temperature, $Ca^{2+}$/$Na^{2+}$ can be altered to reduce the size of cochleate cylinders in the nano-particles containing protein-lipid complex.

The phospholipids useful for the present invention include serine containing compounds including phospholipids. Examples of such serine containing phospholipids are O-Phospho-L-Serine (OPLS), Dicaproyl Phosphatidyl Serine, Dioctanoyl Phosphotidyl Serine, Dimyristoyl, Dipalmitoyl, Dioleoyl-, Disteroyl-Phosphatidyl Serine. The serine containing phsopholipids may be used in combination with other molecules including other phospholipids. For example, phosphatidyl serine can be used in combination with phosphatidyl chloline or Phosphatidyl ethanolamine. In one embodiment, the PS, PC, PA and PE are acylatd or diacylated. The phosphatidyl serine may be obtained from any source such as natural (brain) or from synthetic origin. Phosphatidyl serine may be used in combination with phospatidyl choline (PC). The phosphotidyl choline may be dimyristoyl phophatidyl choline. The ratio of the PS and PC can be varied from 1:9 to 9:1. In one embodiment, the ratio is 3:7.

The protein-lipid compositions of the present invention are preferably stabilized and stored in suitable buffer systems. Such buffers include TRIS buffer and HEPES buffer and sodium and calcium salts. Optionally alcohol (such as 10% ethanol) may be added.

The protein-lipid complexes of the present invention can be characterized by standard methods. For example, fluorescence studies can be carried out on a SLM AMINCO 8000 series instrument or PTI 380 instrument using 4 nm as excitation and emission slits. The samples can be excited at 280 nm and the emission spectra scanned in the range of 300 to 400 nm. The emission spectra of free Factor VIII was observed around 335 nm and the addition of OPLS reduced the intensity of fluorescence emission indicating that the tertiary structure of the protein is altered slightly.

Further, the particle size of the lipid associated protein can be determined using a standard particle sizer (such as NICOMP 315 model). The particle size distribution can be analyzed using both Gaussian and NICOMP analysis for unimoidal and bimoidal distribution. The size of latex beads can be used as standard controls with each measurement.

The lipid structures can also be analyzed by negative staining electron microscopy. Such methods are routine in the art and can be used to confirm that there are no aggregates and to classify the structures as liposomes, non-bilayers or cochleates. The formation of non-bilayer and cochleate structures can also be investigated using Laurdan fluorescence. The lipid structures can be labeled with the probe by mixing the lipid containing solution with aqueous solution of the probe (containing 0.01% ethanol). The samples can be excited at 340 nm and the emission spectra were monitored at 440 nm. The excitation spectra can be acquired in the range of 320 and 420 nm, with emission monochromator at 440 nm.

The protein lipid complexes of the present invention can be delivered to an individual (such as an animal including a human being) by any standard means of administration such as intramuscular, intranasal, intraperitoneal, intravenous, oral, rectal, subcutaneous, topical and the like. The complexes may be delivered directly to or near the target site or may be delivered directly or indirectly into the circulation. The complexes may be delivered in pharmaceutically acceptable carriers which are well known in the art.

The protein-lipid complexes of the present invention exhibit reduced immunogenicity as well as reduced antigenicity. Accordingly, such compositions can be used for reducing immune response in an individual against a therapeutic agent. The compositions of the present invention can also be used for delivery of a therapeutic agent to an individual in whom an immune reaction to the protein has already occurred. Thus, these composition can be used before or after the occurrence of an immune reaction.

In one embodiment, this invention provides specific FVIII-lipid complexes. The protein-lipid complexes may form novel lipidic structures as well as structures such as liposomes, cochleate, micelles and non-bilayer structures to reduce the immune response and antigenicity. The method involves developing specific FVIII-lipid complex preferably stabilized by buffer conditions. Although not intending to be bound by any particular theory, it is believed that the reduction in antigenicity and immunogenecity arise from the protein lipid complex and in molecular assemblies such as liposomes would involve carrier properties such as hydrophobic shielding and cellular (antigen presenting cells APCs) uptake of particulate matters. These complexes have clotting activity in the presence of antibodies and exhibited reduced antigenicity as measured by their ability to bind to monoclonal antibodies in an ELISA assay. The complexes also showed reduced immune response in animal models. The present invention is useful not only to reduce the immune response development in previously untreated patients with FVIII but also retain FVIII clotting activity in previously treated patients who have developed antibodies.

Accordingly, in one embodiment, the present invention provides a method for reducing the immune response against FVIII. By the use of the compositions disclosed herein, immunogenicity is reduced while the clotting activity is maintained. It is considered that the reduction in immunigenicity is accomplished by complexing of the phospholipids with the C2 and A2 domains. It is considered that this decreases immunogenicity by (1) reducing aggregate formation, (2) decreasing the frequency of administration (the complexes alter the clearance mechanism thus by providing longer circulation time) and/or (3) shielding and altering the conformation of the epitope region and/or (4) carrier properties that include preferential cellular uptake. The improved pharmaceutical properties of the complex such as stability, altered clearance mechanism to increase circulation time and reduced antigenicity and immunogenicity is an unexpected observation.

The following examples are presented to further describe the invention and not intended to be restrictive in any way.

EXAMPLE 1

This example demonstrates the preparation of protein-lipid complexes according to present invention. To illustrate this embodiment, FVIII was used. The FVIII-O-phospho-L-serine (OPLS) complex was formed by mixing 20 ug of the protein with 5 and 20 mM of the OPLS in 25 mM TRIS, 300 mM NaCl and 5 mM $CaCl_2$.

EXAMPLE 2

This example describes the stability of the protein-lipid complexes of the present invention (Example. 1). For free FVIII the unfolding of the protein results in the aggregation of the protein and this in turn leads to the irreversibility of unfolding. The aggregation is initiated by small conformational changes in C2 domain. The unfolding/refolding studies were carried out with free FVIII and FVIII complexed to PS as described in Example 1 to determine the stability of the formulation containing protein and O-Phospho-L-Serine that is believed to bind to the C2 domain of FVIII.

Figure 1:
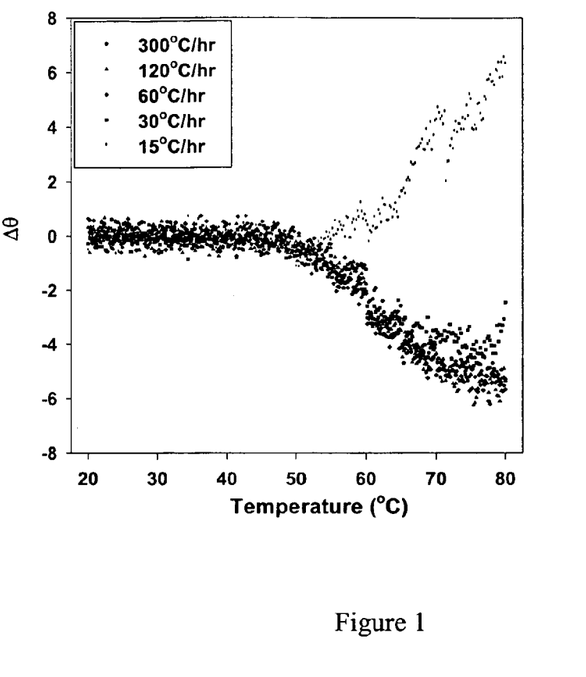
FIG. 1 is the melting profile of FVIII at different heating rates.
Figure 2:
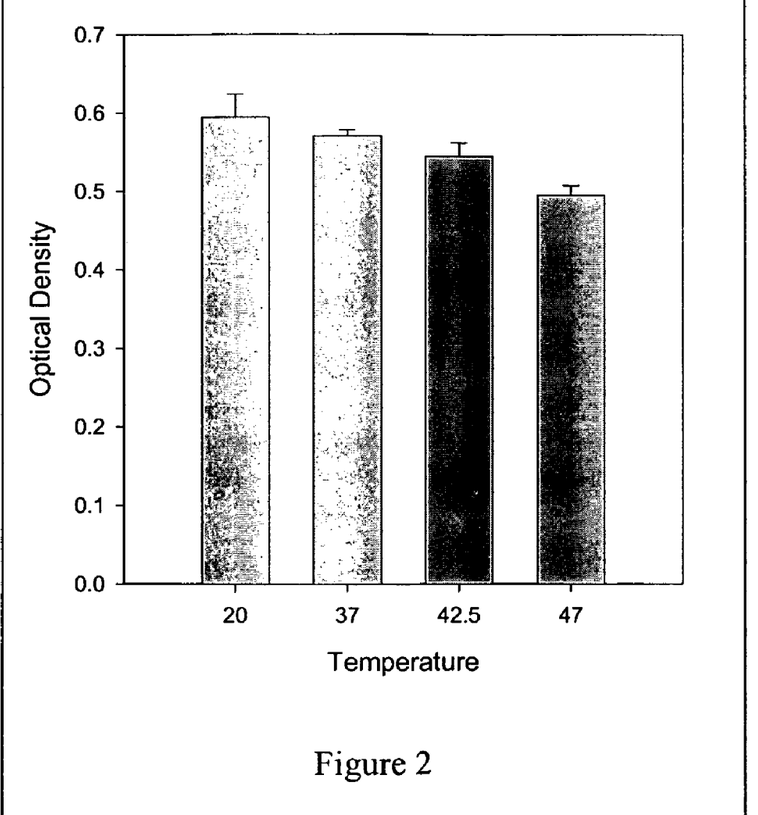
FIG. 2 is the antibody binding assay that shows the conformational changes in the C2 domain. Binding of monoclonal antibodies ESH 4 and ESH8 to rFVIII as determined by sandwich ELISA following the heating of rFVIII at 60° C. and 15° C./hr to the indicated temperatures.
Figure 3:
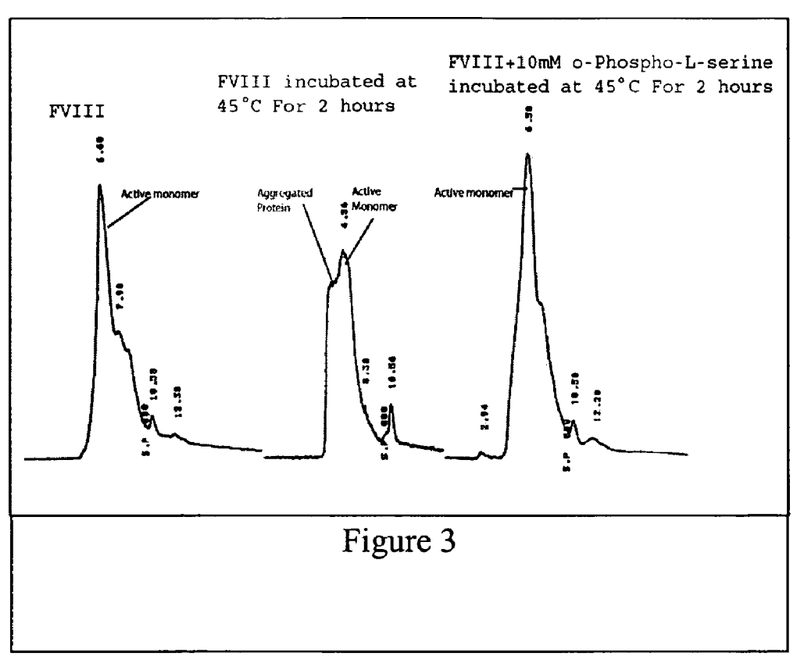
FIG. 3 is a representation of size exclusion chromatography (SEC) profiles of Factor VIII in the presence or absence of O-Phospho-L-Serine.

Circular Dichroism (CD), fluorescence anisotropy, size exclusion chromatography (SEC), domain specific antibody binding and clotting activity studies were carried out to investigate the temperature dependent physical and functional changes of recombinant human FVIII (rFVIII). For determining the folding and unfolding, CD spectral studies were carried out. CD spectra were acquired on a JASCO-715 spectropolarimeter calibrated with d10 camphor sulfonic acid. Samples were scanned in the range of 255 to 208 nm for secondary structure analysis, and typically, the protein concentration used was 20-22 µg/ml. CD spectra of the protein were corrected by subtracting the spectrum of the buffer baseline. Multiple scans were acquired and averaged to improve signal quality. Melting of the protein was followed over the temperature range of 20° C.-80° C. with a 2 min holding time at every 2.5° C. The temperature scans were acquired with a Peltier 300 RTS unit and the profiles were generated using the software provided by the manufacturer. Heating rate dependence of the unfolding profiles indicated that the thermal denaturation of the protein was at least in part under kinetic control (FIG. 1). A folding model was proposed to explain the aggregation kinetics of Factor VIII. Based on this model, unfolding of Factor VIII was interpreted in terms of the simple two-state kinetic model, Aggregated (A)→Native (N) where k is a first-order kinetic constant that changes with temperature, as given by the Arrhenius equation. The activation energy associated with the above transition was calculated to be ~127.98 Kcal/Mole (~534.97 KJ/Mole). Antibody binding studies indicated that conformational changes in the lipid-binding region (2303-2332) of the C2 domain may at least in part be responsible for the initiation of aggregation (FIG. 2). Analysis of the SEC profile of FVIII in the presence and in the absence of OPLS clearly showed that the monomeric population is significantly higher than that of aggregated protein in the presence of PS, possibly due to the interference of OPLS in the aggregation kinetics of Factor VIII (FIG. 3). The data indicates that the complex improves the stability of FVIII and may help to reduce the immunogenecity by reducing the aggregates.

Figure 4:
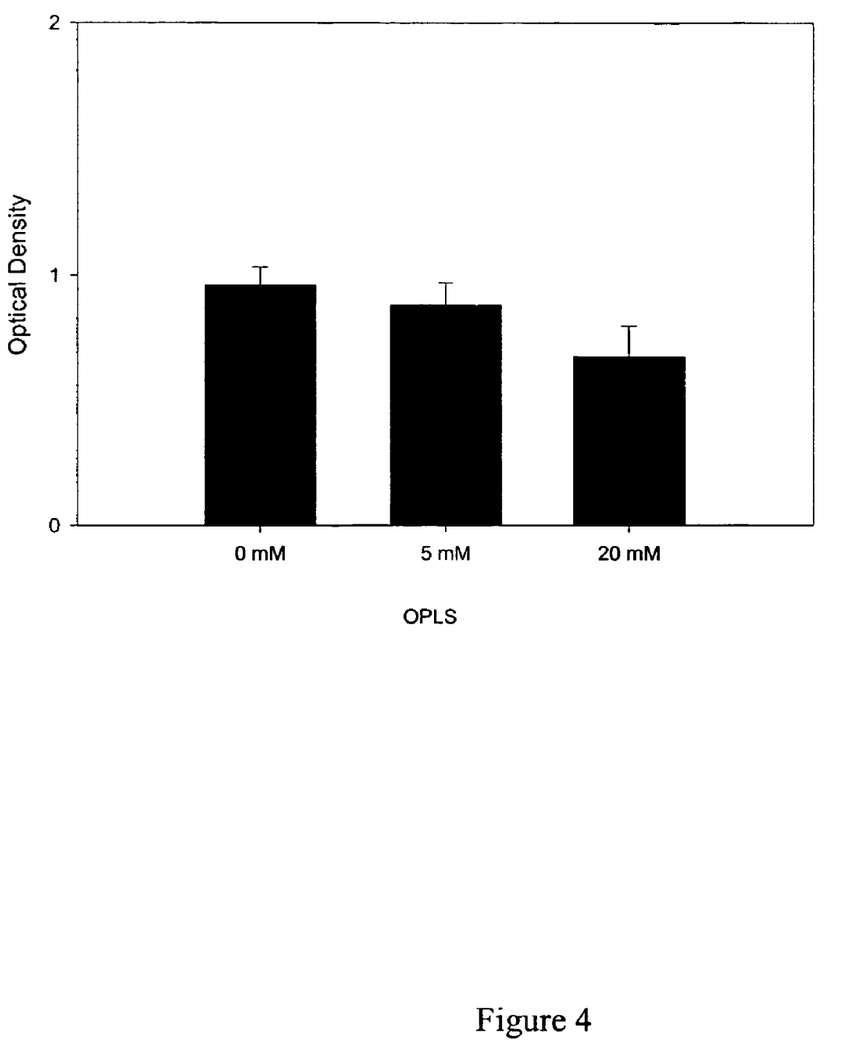
FIG. 4 is a representation of antigenicity of FVIII-O-Phospho-L-Serine studied by sandwich ELISA.

In a further illustration of this embodiment, O-phospho-L-serine was complexed with the protein (likely shielding the C2 domain). 20 ug/ml of the protein was mixed with 5 and 20 mM of phospho-L-serine in different buffers including 25 mM TRIS, 300 mM NaCl and 5 mM CaCl2. The binding to the monoclonal antibodies was studies by sandwich ELISA. As shown in FIG. 4, the recovery of native like structures were not possible for excipient free protein due to aggregation whereas presence of O-Phospho-L-Serine resulted in substantial recovery of native structure.

EXAMPLE 3

This example demonstrates that the protein-lipid composition of the present invention (Example. 1) reduces the immunogenicity against the protein in Sprague-Dawley rats. To illustrate this embodiment, OPLS-Factor VIII complex was administered to Sprague-Dawley rats. This rat model has been shown to be suitable to study antibody development to FVIII. The antibody titer measured by ELISA for free FVIII and FVIII-PS complex. Two weeks after the administration, the analysis of antibody titer for Factor VIII-OPLS complex was found to be non-immunotoxic. The antibody titers for free FVIII is 563.72±916.15 and no detectable antibody titers was observed for FVIII-OPLS complex.

EXAMPLE 4

Figure 5A:
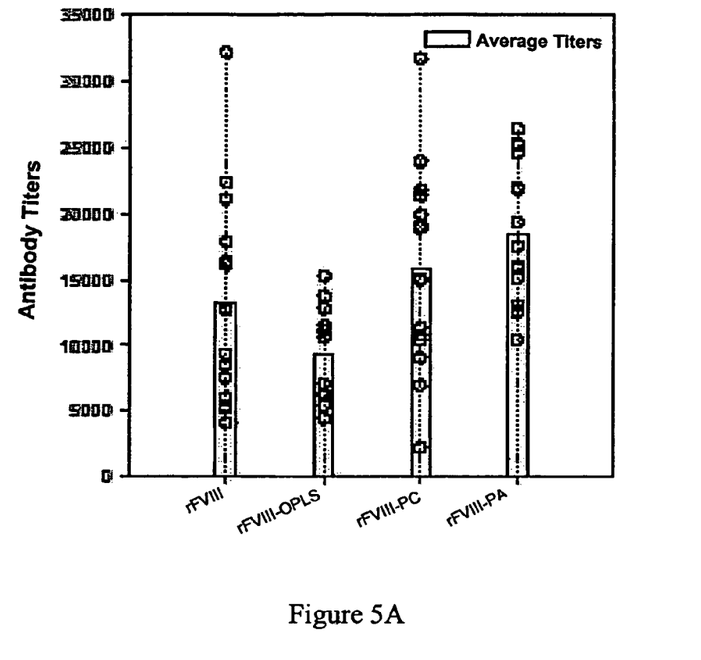
FIGS. 5A and 5B are representation of the effect of OPLS, phosphocholine and phosphatidic acid on the immunogenicity of rFVIII. Average total antibody titres (5A) and inhibitory titres (5B) are shown for the indicated binding agent-rFVIII complexes compared to rFVIII.
Figure 5B:
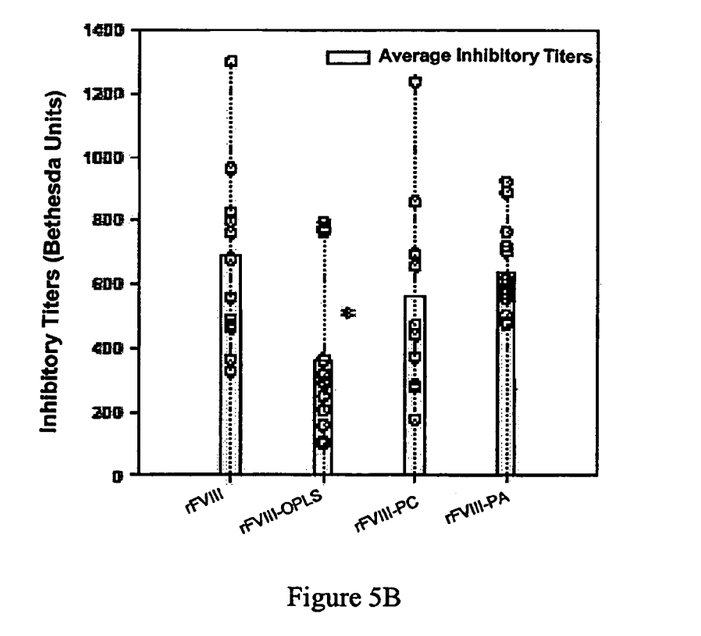

This example demonstrates that phosphoserine is needed in the simple complexes for the reduction in immunogenicity. To illustrate this example, simple complexes were prepared with phosphoserine, phosphocholine or phaphatidic acid. Immunogenicity was tested by subcutaneous administration of the complexes in Hemophilia A mice. The total antibody titers (as measured by ELISA) or specific inhibitory titers (Bethesda Units) titers are shown in FIGS. 5A and 5B. The effect was statistically significant for phosphoserine but not for phosphocholine or phosphatidic acid.

EXAMPLE 5

This example demonstrates that the composition of the present invention can be made as small unilamellar vesicles. 0.3 mg/ml of DMPC and 0.15 mg/ml of bPS dissolved in a round bottomed flask and the solvent was evaporated to form a thin film. The film was then hydrated to form MLV's and the MLVs were extruded through 200 nm polycarbonate filters to form SUV's in the size range of 160 nm. The immune response of this formulation (containing Factor VIII) is described in Example 5.

In all the above mentioned studies, experiments performed using PS free conditions and the concentration of the protein associated with the lipid and lipidic structures are low indicating that the presence of specific lipid-FVIII complex in all these lipidic formulations. Further, the monoclonal antibody specific for C2 domain did not bind to FVIII in the presence of Serine clearly indicates the presence of complex in lipid structures studied.

EXAMPLE 6

Figure 6:
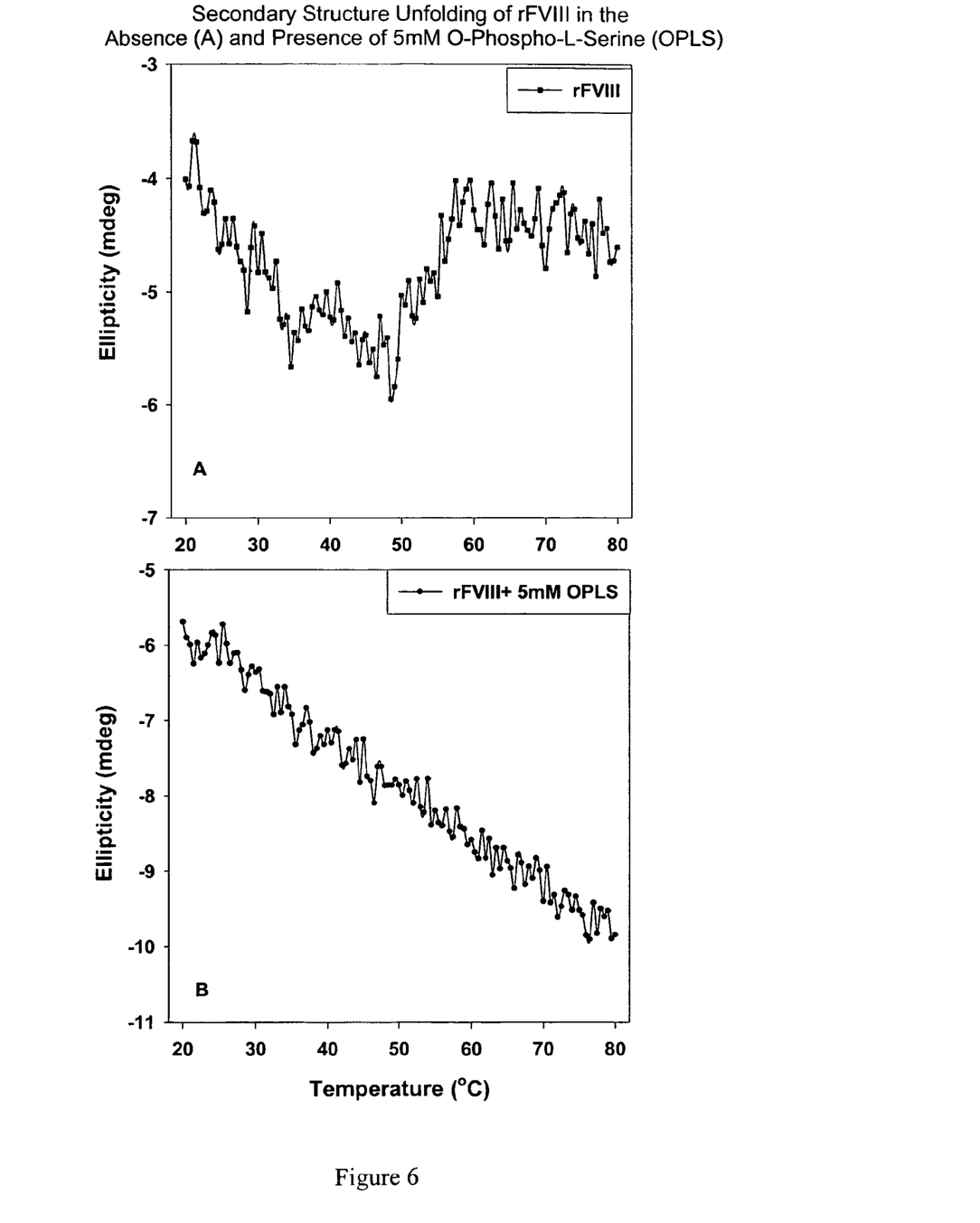
FIG. 6 is a representation of folding studies of FVIII in O phospho L-Serine.
Figure 7:
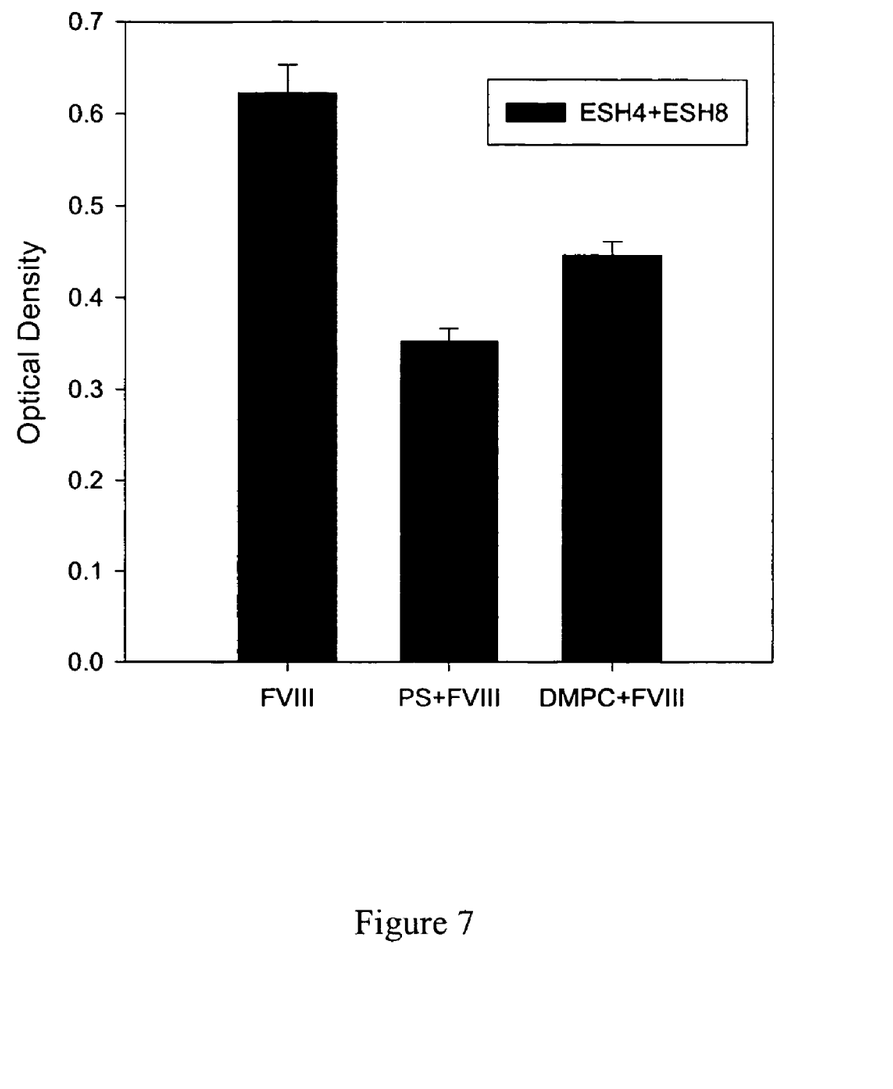
FIG. 7 is a representation of antigenicity of FVIII-PS complex in liposomes studied by sandwich ELISA. FVIII: Free FVIII, Invention FVIII: Composition used in the present invention and DMPC+FVIII: Physical Mixture of DMPC liposomes and FVIII lacking specific protein (FVIII) lipid (PS) complex.

This example demonstrates the general methodology of the ELISA assay to investigate the antigenicity and the participation of particular epitope region of the protein in forming the complex. The antibody binding of the protein-lipid complexes was investigated by antibody capture ELISA and sandwich ELISA. For Sandwich ELISA, 96 well plates (Nunc-Maxisorb) were coated with an anti-C2 domain antibody (ESH4) by incubating 50 µl/well solution of the antibody at a concentration of 5 µg/ml in carbonate buffer (0.2 M, pH 9.4) overnight at 4° C. The plate was then washed 10 times with 100 µl of Phosphate buffer containing 0.05% Tween 20 (PBT consisting of 10 mM $Na_2HPO_4$, 1.8 mM $KH_2PO_4$, 0.14 mM NaCl, 2.7 mM KCl, and 0.02% $NaN_3$). The remaining nonspecific protein binding sites on the plastic's adsorptive surface were blocked by incubating 200 µl of blocking buffer consisting of 1% bovine serum albumin in phosphate buffer (PB consisting of 10 mM $Na_2HPO_4$, 1.8 mM $KH_2PO_4$, 0.14 mM NaCl, and 2.7 mM KCl) for 2 hours at room temperature. The plates were washed 10 times with PBT and 50 µl of 100 ng/ml of rFVIII or rFVIII/OPLS (Examples 1 and 3) or Liposome associated rFVIII (Examples 5) in blocking buffer was added and incubated at 37° C. for 1 hour. The plates were washed 10 times with PBT and incubated with 50 µl of biotinylated ESH8—another anti-C2 antibody, at 1 µg/ml concentration and 50 µl of a 1:1000 dilution of avidin-alkaline phosphatase conjugate, both in blocking buffer at room temperature for 1 hour. The plates were washed 10 times with PBT and 100 µl of 1 mg/ml p-nitrophenyl phosphate solution in diethanolamine buffer (consisting of 1M diethanolamine, 0.5 mM $MgCl_2$ and 0.02% $NaN_3$). The plates were incubated at room temperature for 30 minutes and the reaction was quenched by adding 100 µl of 3 N NaOH. Absorbance was read by a plate reader at 405 nm. The ELISA studies indicated that less C2 domain specific antibodies, ESH8 or ESH4 bound to the protein in the presence of PS (OPLS or liposomes FIG. 6). The results showed that the binding of these monoclonal antibodies were inhibited by lipid suggesting that epitope regions are shielded in the protein-lipid complex. Further, the specific complex FVIII-PS is responsible for the the epitope shielding is further confirmed by the control experiment in which the antigenicity was observed only with DMPC/PS mixture but not with DMPC alone (FIG. 7).

EXAMPLE 7

This example demonstrates that the protein-lipid composition of the present invention (Example. 5) reduces the immunogenicity against the protein in animal models, Sprague-Dawley rats and Factor VIII knock out mice, Hemophilia A model.

Figure 8A:
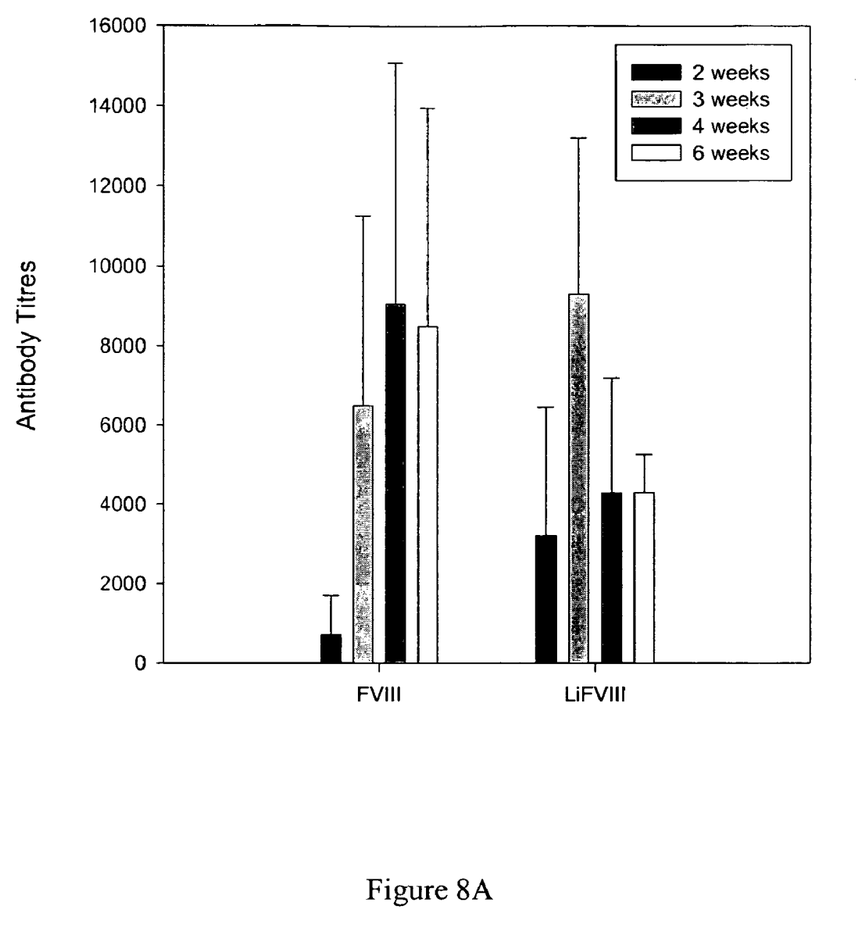
FIG. 8A is a representation of the immune response in animal models for free FVIII and FVIII-PS complex. FVIII: Free FVIII, Invention FVIII: Composition used in the present invention.

The antibody titres evaluated in Sprague-Dawley rats at $4^{th}$ and $6^{th}$ weeks post administration of the protein-liposomes complex was found to be lower for FVIII-PS complex compared to free FVIII (FIG. 8A).

Figure 8B:
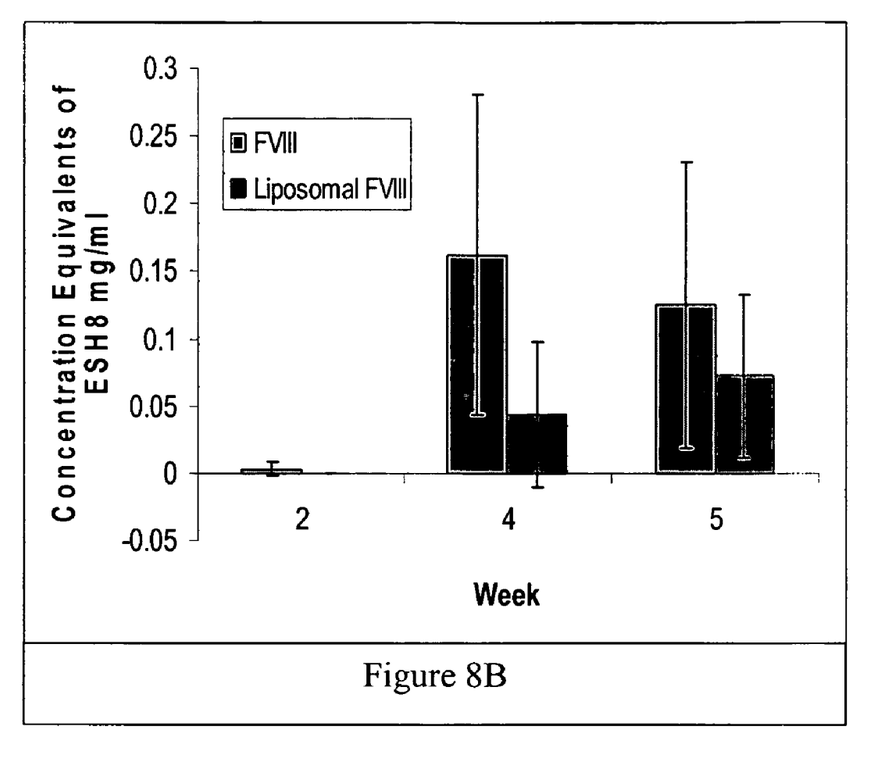
FIG. 8B is a representation of FVII and FVIII-PS complex liposomes in Factor VIII knockout Hemophilia A mice model.

In another illustration of this embodiment, the effect of protein-lipid complexes of the present invention on immunogenicity was tested in a Factor VIII knock out mice model. The phenotype of the mice is severe hemophilia. (exon 16 knock-out by targeted disruption using a neo cassette). The protein-liposome complex (DMPC+bPS) was administered subcutaneously and the antibody titres were measured using ELISA assay. As is clear from the FIG. 8B, the antibody concentrations were lower for the liposome bound protein after 6 weeks of administration. The data clearly demonstrates that liposome bound Factor VIII elicits less antibodies compared to free factor VIII. Although not intending to be bound by any particular theory, this observations may partly be due to altered (1) conformation and aggregation kinetics of free FVIII, (2) decoy effect of particulate material and processing by immune system and (3) clearance mechanism.

EXAMPLE 8

The following examples illustrate the formation of protein-lipid complexes in micelles, non-bilayered structures, cochleate structures and in novel non-liposomal lipid particles. This example describes the formation of micelles by the compositions described herein. The protein solution was mixed with a shorter acyl chain lipids (Dihexanoyl phosphatidyl Serine (below and above 0.3 mM) at lower and higher concentration (below and above critical micellar concentrations) and the resulting micellar particles were characterized. The structure of the micelles were characterized by light scattering, circular dichroism and fluorescence studies. The functional assays such as activity and antibody binding were carried out.

EXAMPLE 9

This example describes the formation of cochleate structures by the compositions described herein. 0.15 mg/ml of bPS was dissolved in chloroform and the solvent was evaporated to form a thin lipid film. The film was then hydrated in several buffer system at pH 7.0 and the MLVs were either extruded or sonicated to form SUVs. The resulting SUVs were mixed with protein in buffer system containing 5 mM $CaCl_2$ to form cochleate structure. The lipid structures were analyzed by light scattering, differential interference microscopy, negative stain electron microscopy and by fluorescence studies. These studies showed that the lipid structures formed by this procedure were cochleate in nature.

EXAMPLE 10

This example is another illustration of the preparation of protein-lipid complexes of the present invention. 0.15 mg/ml of bPS and 0.3 mg.ml of dioleoyl phosphatidylethanolamine (DOPE) was dissolved in chloroform and the solvent was evaporated to form a thin lipid film. The resulting lipid film was hydrated with phosphate buffered saline to form hexagonal phases. The non-bilayer structures were characterized by fluorescence studies.

EXAMPLE 11

Figure 9:
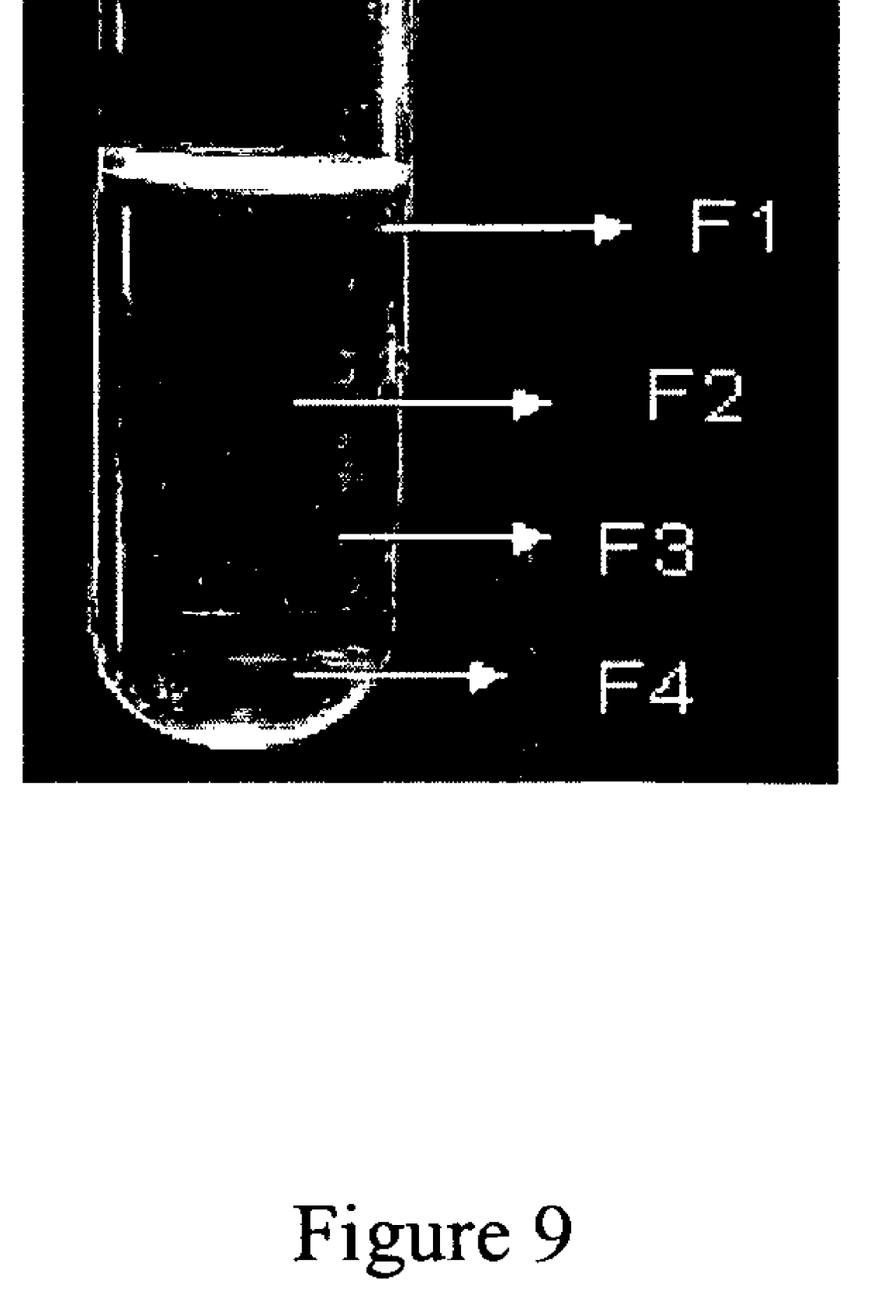
FIG. 9 is the photograph of a Dextran density gradient showing the non-liposomal, low water volume fraction containing FVIII-PS complex.

This example is another illustration of the preparation of protein-lipid complexes of the present invention in a novel non-liposomal structures. 0.3 mg/ml of DMPC, 0.15 mg/ml of bPS were dissolved in chloroform and the solvent was evaporated to form a thin lipid film in a round bottom flask. The lipid was hydrated using a buffer system containing FVIII, 25 mM TRIS, 300 mM NaCl and 5 mM $CaCl_2$ and the solution was gently swirled either at room temperature at 37° C. The film was then hydrated in appropriate buffer (25 mM TRIS, 300 mM NaCl and 5 mM $CaCl_2$), with gentle swirling. The MLV's thus formed were subjected to dextran centrifugation gradient to separate the free protein from protein associated with MLV's. 0.5 ml of the lipid associated protein was mixed with 1 ml of 20% w/v of dextran and a 3ml of 10% w/v dextran was layered over the above solution. Then 0.5 ml of buffer layered on top. The gradient was centrifuged for 35 min at 45K RPM using Beckman SW50.1 rotor. The results of the centrifugation study is shown in FIG. 9. As is clear from the figure, there are some lipidic fractions that could not be floated and are denoted as fraction 3 in the figure. This fraction was observed at the interface of 14% and 10% dextran. The fact that this fraction could not be floated indicates that this lipidic fraction does not have enough buoyancy or encapsulated water. Conventional liposomes generally float to the top of the gradient because of their entrapped water. Therefore, the fraction that does not float may be a non-liposomal protein containing lipidic particles. The fraction was collected and tested for lipid content by mass spectrometry and for protein content by activity. The mass spectroscopy studies showed that this fraction contained lipids including high PC content suggesting that it is not just PS-Ca+ complex. The activity assay showed approximately 40% of the initial protein was encapsulated in this fraction.

There are several possible explanations for the dense fraction 3 which has no or little water content. This fraction may represent: (1) very small unilamellar vesicles with less encapsulated water volume. In order to determine if smaller vesicles (less than 200 nm) could be floated under identical conditions, pre sized liposomes were prepared by extruding through polycarbonate filters. The extrusion was repeated 3 times and the size of the particles was determined to be around 160 nm. The resulting SUVs were mixed with FVIII and were subjected to Dextran centrifugation gradient. This control study showed that these SUV's did not show fraction 3 band indicating that the observation of such bands is not due to the formation of small liposomes. Further, this experiment was performed under identical buffer and experimental conditions to rule out any artifacts in the dextran gradient. (2) The second possibility is that fraction 3 may represent the formation of cochleate structures, which have less water content [26]. However, the formation of cochleate structures needs a very high PS content (>50%). In the formation of fraction 3 band, the PS content used was around 30% and under these conditions the formation of cochleate structures has not been shown. (3) The formation of collapsed Ca(PS)2 complex that has a dehydrated structure [27] may not float and can form a dense band. The formation of such collapsed structure requires very high PS content (>50%) but in the absence of Na+. However, in the present example, the composition contains low PS content and a very high concentration of Na+ i.e., 30% PS and 300 mM NaCl is used and therefore, the possibility of Ca(PS)2 formation is ruled out. (4) The PS and calcium system has been shown to promote vesicle fusion. However, the fusion of vesicles by divalent cations such as $Ca^{2+}$ is inhibited by the presence of Na+ as it competes with calcium for the lipid binding site. The estimated amount of Calcium bound per PS in this PC/PS ratio of 7:3 and in the presence of 300 mM NaCl and 5 mM $CaCl_2$, is between 0.22 (500 mM NaCl) to 0.35 (100 mM NaCl) [28, 29]. This estimated bound calcium per PS is less than the critical ratio of 0.35 to 0.39 required for fusion in a small unilamellar PS/PC vesicle system. Thus, the fusion of vesicles does not appear to be represent the dense band. This is because the larger PC fraction (>50%) may result in less PS-divalent cation complex and its ability to cluster into large domains to induce fusion) [28, 29]. Based on these arguments, it appears that the dense band may be due to the formation of novel, non-liposomal lipid particles. This band is non-liposomal because of less encapsulated water volume. In order to understand the structure of this novel lipidic structure, negative stain electron microscopy, differential contrast interference optical microscopy, light scattering, circular dichroism and fluorescence measurements (data not shown) were performed.

Centrifugation studies carried out under several conditions indicate that buffer conditions, bulk protein concentration, use of alochol (such as 10% ethanol) and protein-lipid ratio can be varied to obtain the desired yield of the complexes. Such variations in these parameters are considered to be within the purview of one skilled in the art. In general, it was observed that higher protein concentration resulted in more intense dense fraction as confirmed by visual inspection.

EXAMPLE 12

This example demonstrates that the protein-lipid compositions of the present invention retain their biological activity. To illustrate this embodiment, the effect of protein-lipid complex (OLPS, DCPS, and DCPC) comprising Factor VIII on clotting was tested. rFVIII clotting activity was determined by one-stage activated partial thromboplastin time (APTT) assay using micronized silica as activator and FVIII deficient plasma as the substrate. The APTT assay was performed using a COAG-A-MATE model coagulation analyzer (Organon Teknika Corporation, Durham, N.C.). Briefly, rFVIII was added to FVIII deficient plasma and the clotting time was monitored. The activity of the rFVIII was then obtained from calibration curve constructed using the clotting times determined from various dilutions of a lyophilized reference concentrate of known activity. The concentration of the protein was determined independently using Bicinchoninic acid (BCA) assay and compared with activity. For example, all the 20-22 µg/ml of the protein corresponds to specific activity of 87-95.6 IU. The stock solution used to prepare the samples had a specific activity of 2174 IU/0.5 mg/ml.

EXAMPLE 13

Figure 10:
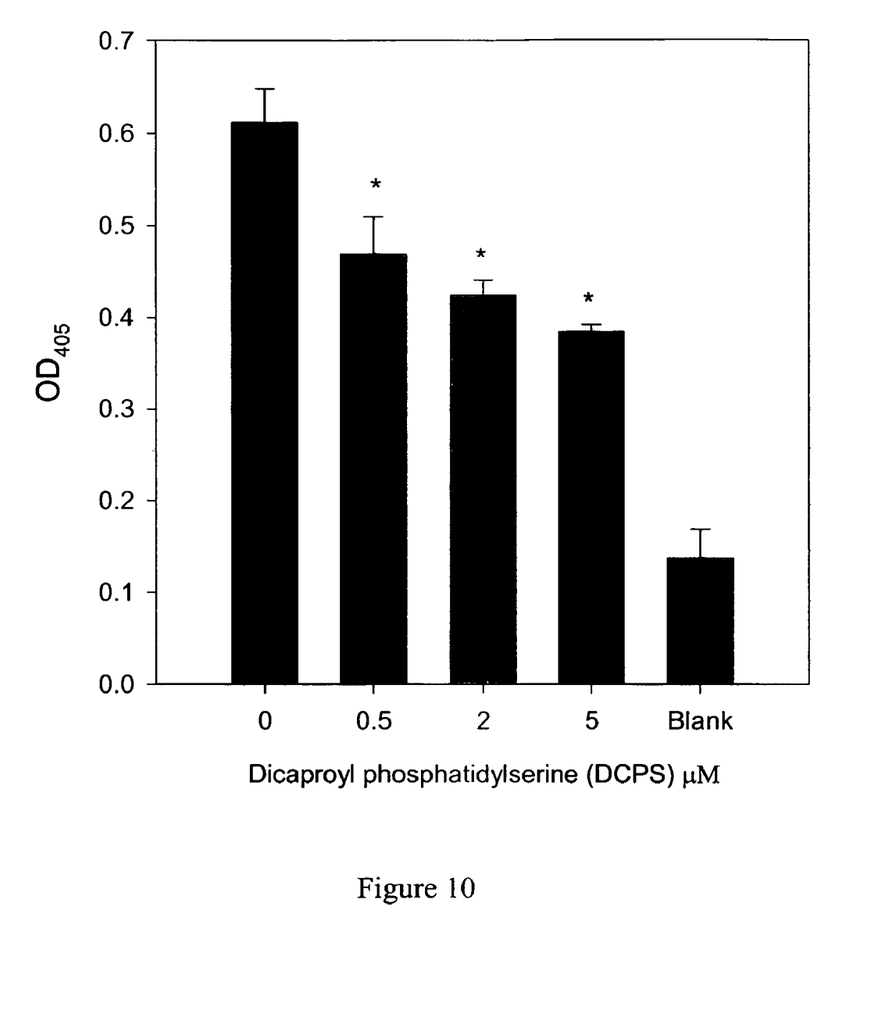
FIG. 10 is a representation of the effect of DCPS on the antigenicity of rFVIII

This example demonstrates reduced antigenicity of proteins in the presence of PS containing phospholipids. To illustrate this embodiment, the effect of dicaproyl phopatidylserine (DCPS) on the binding of rFVIII to ESH4 antibody was tested. The FVIII-(DCPS) complex was formed by mixing 2 ug of the protein with 0.5, 2 and 5 mM of the DCPS in 25 mM TRIS, 300 mM NaCl and 5 mM CaCl2. The antigenicity of the complex was investigated using ELISA. As shown in FIG. 10, DCPS inhibited the binding of rFVIII to ESH4 antibody at the concentrations tested i.e., 0.5, 2 and 5.0 uM. These concentrations are above and below the CMC of this phospholipid.

EXAMPLE 14

This example describes the effect of PS containing phospholipids on the immunogenicity of proteins. The FVIII-(DCPS) complex was formed by mixing 2 ug of the protein with 5 mM of DCPS in 25 mM TRIS, 300 mM NaCl and 1 mM CaCl2. This composition forms micellar structure and the immunogenicity of the complex was investigated in Hemophilia A mice. The total antibody titers for free FVIII is 13,167 (SD=7909, n=16) and for FVIII-DCPS complex is 3506 (SD=1150.7, n=12).

EXAMPLE 15

The FVIII-Dicaproyl Phosphatidyl Choline (DCPC) complex was formed by mixing 2 ug of the protein with 20 mM of DCPC in 25 mM TRIS, 300 mM NaCl and 1 mM CaCl2. This composition forms micellar structure and the immunogenicity of the complex was investigated in Hemophilia A mice. The total antibody titers for free FVIII is 13,167 (SD=7909, n=16) and for FVIII-DCPC complex is 1293 (SD=946.57, n=12).

EXAMPLE 16

This example demonstrates that the composition of the present invention can be made as liposomal vesicles. 11.25µmol of DMPC and 4.83 µmol of BPS dissolved in choloroform were taken in a round-bottomed flask and the solvent was evaporated using a rota-evaporator to form a thin film on the walls of the flask. The film was then hydrated in 3 ml Tris buffer (containing 300 mM NaCl, 25 mM Tris, 5 mM $CaCl_2$, pH=7.0) to form MLV's and the MLVs were extruded through either 80 nm or 200 nm or 400 nm polycarbonate filters to form SUV's in the size range of 80 nm to 400 nm. Lipid recovery was estimated by determination of phosphorous content by the method of Bartlett. The protein was associated with liposomes by incubating at 37° C. for 30 minutes. The liposomes were then be used in immunizations as follows. Immunization of FVIII knockout mice consisted of four subcutaneous (s.c.) injections of rFVIII or rFVIII-liposomes (2 µg in 100 µl of Tris buffer) at weekly intervals. The molar ratio between the protein and lipid was maintained at 1:10,000.

In another sample, 11.25 µmol of DMPC dissolved in choloroform was taken in a round-bottomed flask and the solvent was evaporated using a rota-evaporator to form a thin film on the walls of the flask. The film was then hydrated with 3 ml Tris buffer (containing 300 mM NaCl, 25 mM Tris, 5 mM $CaCl_2$, pH=7.0) to form MLV's and the MLVs were extruded through either 80 nm or 200 nm or 400 nm polycarbonate filters to form SUV's in the size range of 80 nm to 400 nm. Lipid recovery was estimated by determination of phosphorous content by the method of Bartlett. The protein was associated with liposomes by incubating at 37° C. for 30 minutes. Immunization of FVIII knockout mice consisted of four subcutaneous (s.c.) injections of rFVIII or rFVIII-liposomes (2 µg in 100 µl of Tris buffer) at weekly intervals. The molar ratio between the protein and lipid was maintained at 1:10,000. DSPC having a high phase transition temperature (solid state) was used a negative control.

In another sample, 7.5 µmol of DMPC and 3.22 µmol of DOPA dissolved in choloroform were taken in a round-bottomed flask and the solvent was evaporated using a rota-evaporator to form a thin film on the walls of the flask. The film was then hydrated with 2 ml Tris buffer (containing 300 mM NaCl, 25 mM Tris, 5 mM $CaCl_2$, pH=7.0) to form MLV's and the MLVs were extruded through 200 nm polycarbonate filters to form SUV's in the size range of ~200 nm. Lipid recovery was estimated by determination of phosphorous content by the method of Bartlett. The protein was associated with liposomes by incubating at 37° C. for 30 minutes. Immunization of FVIII knockout mice consisted of four subcutaneous (s.c.) injections of rFVIII or rFVIII-liposomes (2 µg in 100 µl of Tris buffer) at weekly intervals. The molar ratio between the protein and lipid was maintained at 1:10,000.

In another sample, 7.5 µmol of DMPC and 3.22 µmol of DOPG dissolved in choloroform were taken in a round-bottomed flask and the solvent was evaporated using a rota-evaporator to form a thin film on the walls of the flask. The film was then hydrated with 2 ml Tris buffer (containing 300 mM NaCl, 25 mM Tris, 5 mM $CaCl_2$, pH=7.0) to form MLV's and the MLVs were extruded through 200 nm polycarbonate filters to form SUV's in the size range of ~200 nm. Lipid recovery was estimated by determination of phosphorous content by the method of Bartlett. The protein was associated with liposomes by incubating at 37° C. for 30 minutes. Immunization of FVIII knockout mice consisted of four subcutaneous (s.c.) injections of rFVIII or rFVIII-liposomes (2 μg in 100 μl of Tris buffer) at weekly intervals. The molar ratio between the protein and lipid was maintained at 1:10,000. The immune response of this formulation is described in Table 1.

TABLE 1

| Composition | Size* (nm) | Lamellar Phase State at 37° C. | Total Anti-rFVIII Antibody Titers (Mean ± S.E.M) | Anti-rFVIII Inhibitory Titers (BU/ml)(Mean ± S.E.M) |
|---|---|---|---|---|
| 1. rFVIII (Control) | — | — | 13166.7 ± 2042.2 (n = 15) | 689.7 ± 78.2 (n = 13) |
| 2. DMPC/BPS | 200 | Fluid | 5699.9 ± 1254.7 (n = 15)** | 215.4 ± 70.9 (n = 14)** |
| 3. DMPC | 200 | Fluid | 6075.3 ± 1114.4 (n = 15)** | 271.3 ± 82.1 (n = 14)** |
| 4. DMPC/DOPA | 200 | Fluid | 5640.4 ± 1208.1 (n = 15)** | 185.4 ± 53.6 (n = 13)** |
| 5. DMPC/DOPG | 200 | Fluid | 5592.4 ± 950.3 (n = 15)** | 299.2 ± 87.9 (n = 14)** |
| 6. DMPC | 400 | Fluid | 6403 ± 1730 (n = 12)** | 245.0 ± 72.1 (n = 12)** |
| 7. DMPC/BPS | 400 | Fluid | 4030 ± 495.8 (n = 12)** | 160.6 ± 27.3 (n + 12)** |
| 8. DMPC | 80 | Fluid | 9680.6 ± 2585.9 (n = 12) | 261.5 ± 53.2 (n = 12)** |
| 9. DMPC/BPS | 80 | Fluid | 7056.6 ± 806.9 (n = 12)** | 257.7 ± 35.4 (n = 12)** |
| 10. DSPC | 200 | Gel | 9823.7 ± 1401.9 (n = 12) | 532.2 ± 111.8 (n = 12) |

Mean total anti-rFVIII antibody titers and inhibitory titers following immunization of FVIII-KO mice with rFVIII in the absence and presence of liposomes at the end of six weeks. *, indicates the pore size of polycarbonate membranes used to extrude liposomes, **$p < 0.05$, statistical analysis was carried out as described under Experimental Procedures.

While this invention has been described through examples presented herein, routine modifications can be made to the invention without departing from the spirit of the invention. Such modifications are intended to be within the scope of the claims.

REFERENCES

1. Fay, P. J. Factor VIII structure and function. *Thromb Haemost* 70, 63-7 (1993).
2. Foster, P. A. & Zimmerman, T. S. Factor VIII structure and function. *Blood Rev* 3, 180-91 (1989).
3. Braun, A., Kwee, L., Labow, M. A. & Alsenz, J. Protein aggregates seem to play a key role among the parameters influencing the antigenicity of interferon alpha (IFN-alpha) in normal and transgenic mice. *Pharmaceutical Research* 14, 1472-8 (1997).
4. Grillo, A. O. et al. Conformational origin of the aggregation of recombinant human factor VIII. *Biochemistry* 40, 586-95 (2001).
5. Scandella, D. H. et al. In hemophilia a and autoantibody inhibitor patients: the factor viii a2 domain and light chain are most immunogenic. *Thromb Res* 101, 377-85. (2001).
6. Lenting, P. J. et al. The light chain of factor VIII comprises a binding site for low density lipoprotein receptor-related protein. *Journal of Biological Chemistry.* 274, 23734-9 (1999).
7. Saenko, E. L., Yakhyaev, A. V., Mikhailenko, I., Strickland, D. K. & Sarafanov, A. G. Role of the low density lipoprotein-related protein receptor in mediation of factor VIII catabolism. *Journal of Biological Chemistry.* 274, 37685-92 (1999).
8. Gilbert, G. E., Furie, B. C. & Furie, B. Binding of human factor VIII to phospholipid vesicles. *J Biol Chem* 265, 815-22 (1990).
9. Stoilova-McPhie, S., Villoutreix, B. O., Mertens, K., Kemball-Cook, G. & Holzenburg, A. 3-Dimensional structure of membrane-bound coagulation factor VIII: modeling of the factor VIII heterodimer within a 3-dimensional density map derived by electron crystallography. *Blood* 99, 1215-23. (2002).
10. Scandella, D. et al. Some factor VIII inhibitor antibodies recognize a common epitope corresponding to C2 domain amino acids 2248 through 2312, which overlap a phospholipid-binding site. *Blood* 86, 1811-9. (1995).
11. Barrow, R. T., Healey, J. F., Jacquemin, M. G., Saint-Remy, J. M. & Lollar, P. Antigenicity of putative phospholipid membrane-binding residues in factor VIII. *Blood* 97, 169-74. (2001).
12. Kirby, C. J. & Gregoriadis, G. Preparation of liposomes containing factor VIII for oral treatment of haemophilia. *J Microencapsul* 1, 33-45. (1984).
13. Hemker, H. C., Hermens, W. T., Muller, A. D. & Zwaal, R. F. Oral treatment of haemophilia A by gastrointestinal absorption of factor VIII entrapped in liposomes. *Lancet* 1, 70-1. (1980).
14. Martin, F. J., Hubbell, W. L. & Papahadjopoulos, D. Immunospecific targeting of liposomes to cells: a novel and efficient method for covalent attachment of Fab' fragments via disulfide bonds. *Biochemistry* 20, 4229-38. (1981).
15. Matthay, K. K., Heath, T. D., Badger, C. C., Bernstein, I. D. & Papahadjopoulos, D. Antibody-directed liposomes: comparison of various ligands for association, endocytosis, and drug delivery. *Cancer Res* 46, 4904-10. (1986).
16. Olson, F., Hunt, C. A., Szoka, F. C., Vail, W. J. & Papahadjopoulos, D. Preparation of liposomes of defined size distribution by extrusion through polycarbonate membranes. *Biochim Biophys Acta* 557, 9-23. (1979).
17. Papahadjopoulos, D. et al. Sterically stabilized liposomes: improvements in pharmacokinetics and antitumor therapeutic efficacy. *Proc Natl Acad Sci USA* 88, 11460-4 (1991).
18. Phillips, N. C. & Emili, A. Enhanced antibody response to liposome-associated protein antigens: preferential stimulation of IgG2a/b production. *Vaccine* 10, 151-8. (1992).
19. Storm, G., Wilms, H. P. & Crommelin, D. J. Lippsomes and biotherapeutics. *Biotherapy* 3, 25-42 (1991).
20. Szoka, F., Jr. & Papahadjopoulos, D. Procedure for preparation of liposomes with large internal aqueous space and high capture by reverse-phase evaporation. *Proc Natl Acad Sci USA* 75, 4194-8. (1978).
21. Szoka, F. et al. Preparation of unilamellar liposomes of intermediate size (0.1-0.2 mmol) by a combination of reverse phase evaporation and extrusion through polycarbonate membranes. *Biochim Biophys Acta* 601, 559-71. (1980).
22. Van Slooten, M. L. et al. Liposomes as sustained release system for human interferon-gamma: biopharmaceutical aspects. *Biochim Biophys Acta* 1530, 134-45. (2001).
23. Papahadjopoulos, D., Vail, W. J., Jacobson, K. & Poste, G. Cochleate lipid cylinders: formation by fusion of unilamellar lipid vesicles. *Biochim Biophys Acta* 394, 483-91. (1975).
24. Coorssen, J. R. & Rand, R. P. Structural effects of neutral lipids on divalent cation-induced interactions of phosphatidylserine-containing bilayers. *Biophys J* 68, 1009-18. (1995).
25. Duzgunes, N. et al. Calcium- and magnesium-induced fusion of mixed phosphatidylserine/phosphatidylcholine vesicles: effect of ion binding. *J Membr Biol* 59, 115-25. (1981).
26. Duzgunes, N., Wilschut, J., Fraley, R. & Papahadjopoulos, D. Studies on the mechanism of membrane fusion. Role of head-group composition in calcium- and magnesium-induced fusion of mixed phospholipid vesicles. *Biochim Biophys Acta* 642, 182-95. (1981).
27. Alving, C. R., Liposomes as carriers of antigens and adjuvants. J. Immunol. Methods, 140:1-13, (1991).
28. Van Rooijen, N., Liposomes as carrier and immunoadjuvant of vaccine antigens. Adv. Biotechnolo Processes, 13: 255-279 (1990).
29. Huong, T. M., Ishida, T., Harashima, H. & Kiwada, H. The complement system enhances the clearance of phosphatidylserine (PS)-liposomes in rat and guinea pig. *Int J Pharm* 215, 197-205. (2001).
30. Dal Monte, P. & Szoka, F. C., Jr. Effect of liposome encapsulation on antigen presentation in vitro. Comparison of presentation by peritoneal macrophages and B cell tumors. *J Immunol* 142, 1437-43. (1989).
31. Heath, T. D., Edwards, D. C. & Ryman, B. E. The adjuvant properties of liposomes. *Biochemical Society Transactions* 4, 129-33 (1976).
32. Rosenblum et al., Modified Proteins, designer toxins, and methods of making thereof, U.S. patent application publication 20030176331, 2003.

The invention claimed is:

1. A method for reducing the immunogenicity of Factor VIII comprising the steps of forming a complex of Factor VIII with a binding agent, wherein the binding agent is O-Phospho-L-Serine (OPLS), wherein the immunogenicity of Factor VIII upon administration to an individual is reduced when complexed with the binding agent.

* * * * *